(12) United States Patent
Mita et al.

(10) Patent No.: US 9,193,684 B2
(45) Date of Patent: Nov. 24, 2015

(54) COMPOUND, OPTICAL RESOLUTION METHOD, AND DERIVATIVE OF AN OPTICAL ISOMER OF AN AMINO ACID

(71) Applicants: SHISEIDO COMPANY, LTD., Tokyo (JP); KYUSHU UNIVERSITY, NATIONAL UNIVERSITY CORPORATION, Fukuoka (JP)

(72) Inventors: Masashi Mita, Tokyo (JP); Kenji Hamase, Fukuoka (JP); Tsubasa Oyama, Fukuoka (JP)

(73) Assignees: SHISEIDO COMPANY, LTD., Tokyo (JP); KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 0 days.

(21) Appl. No.: 14/472,920

(22) Filed: Aug. 29, 2014

(65) Prior Publication Data
US 2015/0065716 A1   Mar. 5, 2015

(30) Foreign Application Priority Data
Sep. 2, 2013  (JP) ................. 2013-181305

(51) Int. Cl.
C07D 215/22  (2006.01)
C07D 401/12  (2006.01)
C07C 227/34  (2006.01)

(52) U.S. Cl.
CPC ............ C07D 215/22 (2013.01); C07C 227/34 (2013.01); C07D 401/12 (2013.01)

(58) Field of Classification Search
CPC .............................. C07D 215/22; C07D 401/12
See application file for complete search history.

(56) References Cited

FOREIGN PATENT DOCUMENTS
WO    2008144865    * 12/2008

OTHER PUBLICATIONS
K. Shimbo et al., Multifunctional and Highly Sensitive Precolumn Reagents for Amino Acids in Liquid Chromatography/Tandem Mass Spectrometry, Anal. Chem., 2009, 81, 5172-5179.

K. Shimbo et al., Precolumn derivatization reagents for high-speed analysis of amines and amino acids in biological fluid using liquid chromatography/electrospray ionization tandem mass spectrometry, Rapid Commun. Mass Spectrom., 2009; 23; 1483-1492.

S. A. Cohen et al., Synthesis of a Fluorescent Derivatizing Reagent, 6-Aminoquinolyl-N-Hydroxysuccinimidyl Carbamate, and Its Application for the Analysis of Hydrolysate Amino Acids via High-Performance Liquid Chromatography, Analytical Biochemistry, 211, 279-287 (1993).

R. J. Reischl et al., Methoxyquinoline labeling—A new strategy for the enantioseparation of all chiral proteinogenic amino acids in 1-dimensional liquid chromatography using fluorescence and tandem mass spectrometric detection, Journal of Chromatography A, 1269 (2012) 262-269.

* cited by examiner

*Primary Examiner* — D M Seaman
(74) *Attorney, Agent, or Firm* — IPUSA, PLLC

(57) ABSTRACT

Disclosed is a compound represented by chemical formula (1):

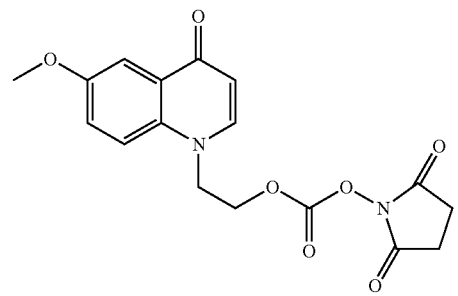

or chemical formula (2):

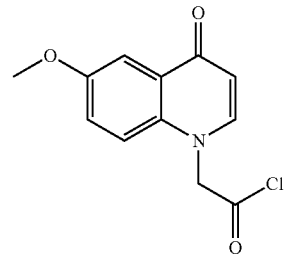

1 Claim, 5 Drawing Sheets

COMPOUND, OPTICAL RESOLUTION METHOD, AND DERIVATIVE OF AN OPTICAL ISOMER OF AN AMINO ACID

BACKGROUND OF THE INVENTION

1. Field of the Invention

One aspect of the present invention relates to at least one of a compound, an optical resolution method, and a derivative of an optical isomer of an amino acid.

2. Description of the Related Art

Conventionally, it has been considered that amino acids present in a living body of a higher animal are only L-amino acids. However, it is found that D-amino acids are also present in a living body, due to development of an analysis technique in recent years.

From the viewpoint of elucidating of a physiological role of an amino acid in a living body, development and study of an analytical technique for precisely quantifying an amino acid (see, for example, K. Shimbo et al., Anal. Chem., 2009, 81, 5172-5179; K. Shimbo et al., Rapid Commun. Mass Spectrom., 2009, 23, 1483-1492; and S. A. Cohen et al., Anal. Biochem., 1993, 211, 279-287) or a D-amino acid and an L-amino acid (see, for example, R. J. Reischl et al., J. Chromatogra. A., 2012, 1269, 262-269) are being advanced by utilizing high-performance liquid chromatography (HPLC).

However, an optical resolution method as described in K. Shimbo et al., Anal. Chem., 2009, 81, 5172-5179; K. Shimbo et al., Rapid Commun. Mass Spectrom., 2009, 23, 1483-1492; S. A. Cohen et al., Anal. Biochem., 1993, 211, 279-287; or R. J. Reischl et al., J. Chromatogra. A., 2012, 1269, 262-269 has a problem that a performance and a sensitivity of optical resolution are low. Furthermore, in order to prepare an analytical sample, it is necessary to conduct a reaction between a mixture of optical isomers of an amino acid and a compound for optical resolution for a comparatively long period of time while heat is applied thereto.

SUMMARY OF THE INVENTION

According to one aspect of the present invention, there is provided a compound represented by chemical formula (1):

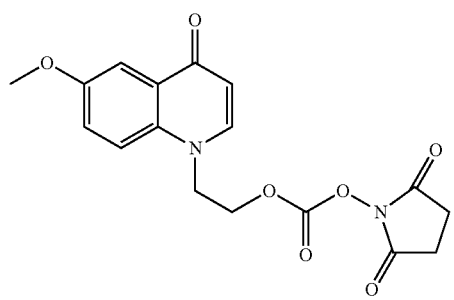 [SMILES: COc1ccc2c(c1)c(=O)ccn2CCOC(=O)ON1C(=O)CCC1=O]

or chemical formula (2):

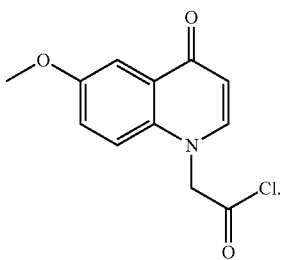 [SMILES: COc1ccc2c(c1)c(=O)ccn2CC(=O)Cl]

According to another aspect of the present invention, there is provided an optical resolution method, including a first step of mixing optical isomers of an amino acid with the compound as described above to obtain derivatives of the optical isomers.

According to another aspect of the present invention, there is provided a derivative of an optical isomer of an amino acid obtained by the optical resolution method as described above.

DETAILED DESCRIPTION OF THE PREFERRED EMBODIMENTS

An embodiment of the present invention will be described in detail below. Here, although an embodiment that uses an amino acid as a target for optical resolution is primarily described in the present specification, it is possible for a compound for optical resolution according to an embodiment of the present invention to conduct optical resolution at a high sensitivity, even for another target for optical resolution such as an amine, an alcohol, a thiol, or a carboxylic acid.

(A Compound for Optical Resolution)

The inventors have found that a performance of optical resolution of an amino acid is significantly improved by using a reagent for optical resolution (or a kit for optical resolution) that includes a compound represented by structural formula (1) or structural formula (2) described below to derivatize a mixture of optical isomers of an amino acid in a technique of optical resolution of an amino acid or the like in an HPLC method.

Chemical formula 1

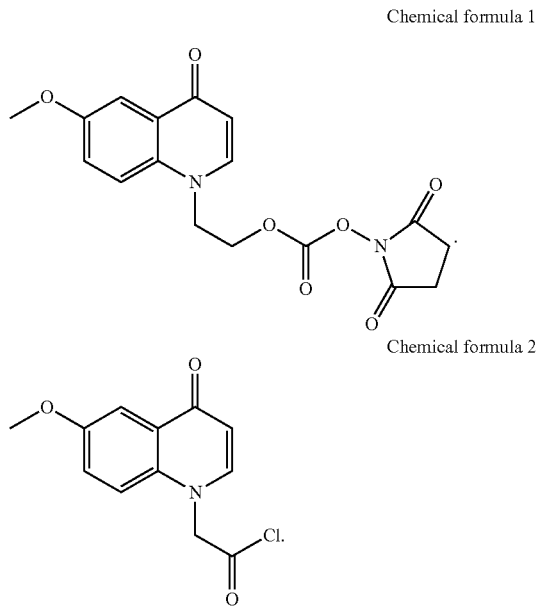

Chemical formula 2

A detail of a reason why a performance of optical resolution in an HPLC method is improved by using a compound with a structural formula (1) or structural formula (2) to derivatize an amino acid is under investigation. However, as derivatization is conducted by using these compounds, it is possible to conduct optical resolution of an obtained amino acid derivative in an HPLC method at a high sensitivity. Furthermore, it has also been found that it is possible for a compound with structural formula (1) or structural formula (2) described above to derivatize an amino acid in a short period of time and an obtained amino acid derivative has excellent heat stability and light stability.

(An Example of Synthesis of a Compound for Optical Resolution with Structural Formula (1))

Figure 1:
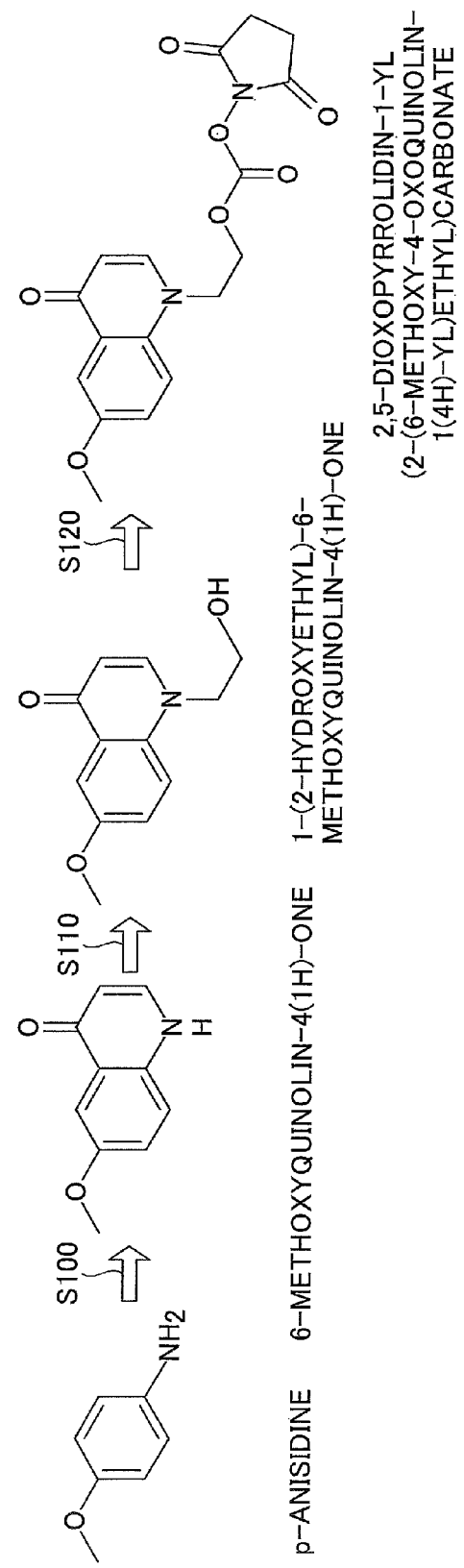
FIG. 1 is one example of a synthetic scheme for a compound for optical resolution according to the present embodiment.

FIG. 1 illustrates one example of a synthetic scheme of a compound for optical resolution according to the present embodiment. A specific example of synthesis of a compound for optical resolution with structural formula (1) will be described below, with reference to FIG. 1.

4.32 parts of diethyl ethoxymethylenemalonate were added to 2.45 parts of p-anisidine, and heating and stirring thereof were conducted at 110° C. for 2 hours by using an oil bath under a nitrogen stream. Then, 20 ml of diphenyl ether were added thereto, and reflux thereof was conducted for 1 hour by using a mantle heater. After standing to cool to room temperature, hexane was added to a reaction solution to filtrate and obtain a precipitate and an obtained product was washed with acetone.

15 ml of a 1 M aqueous solution of sodium hydroxide were added to this product and reflux thereof was conducted for 1 hour. After a reaction solution was acidized with an aqueous solution of hydrochloric acid, a precipitate was filtrated and obtained and an obtained product was washed with water.

Then, 20 ml of diphenyl ether were added to this product, and reflux thereof was conducted for 1.5 hours under a nitrogen stream by using a mantle heater. After standing to cool to room temperature, hexane was added to a reaction solution to filtrate and obtain a precipitate and an obtained product was washed with acetone to obtain a white powder (S100). An obtained powder was identified by $^1$H NMR as 6-methoxyquinolin-4(1H)-one. Here, in the present specification, $^1$H NMR was conducted at a strength of electric field of 400 mega-heltz (MHz).

Here, a result of $^1$H NMR measurement was: $^1$H NMR (dmso): δ 3.817 (3H, s), 5.975 (1H, d, J=7.6 Hz), 7.270 (1H, dd, J=3.2, 9.2 Hz), 7.477 (1H, s), 7.492 (1H, d, J=5.6 Hz), 7.818 (1H, s), 11.676 (1H, s).

526 parts of obtained 6-methoxyquinolin-4(1H)-one, 107 parts of potassium hydroxide, and 798 parts of ethylene carbonate were dissolved in 5 ml of N,N-dimethylformamide (DMF), and heating and stirring thereof were conducted at 130° C. overnight by using an oil bath under a nitrogen stream. After completion of a reaction, a solvent in a reaction solution was removed under a reduced pressure. An obtained residue was fractionated by silica gel column chromatography (developing solvent; chloroform:methanol=20:1→10:1) to obtain a white powder (S110). An obtained powder was identified by $^1$H NMR as 1-(2-hydroxyethyl)-6-methoxyquinolin-4(1H)-one. Here, it is preferable for a white powder of 1-(2-hydroxyethyl)-6-methoxyquinolin-4(1H)-one to be subjected to a recrystallization process that uses chloroform or ethanol, in order to improve a purity thereof, and to be supplied to a next step as a needle crystal.

Here, a result of $^1$H NMR measurement was: $^1$H NMR (dmso): δ 3.695 (2H, q, J=5.6, 5.2 Hz), 3.835 (3H, s), 4.270 (2H, t, J=5.2 Hz), 4.926 (1H, t, J=5.2 Hz), 5.981 (1H, d, J=7.6 Hz), 7.318 (1H, dd, J=2.8, 9.4 Hz), 7.599 (1H, d, J=3.6 Hz), 7.708 (1H, d, J=9.6 Hz), 7.824 (1H, d, J=7.6 Hz).

1 part by mass of di(N-succinimidyl) carbonate was dissolved in 10 ml of dichloromethane and 2 ml of pyridine was added thereto. After 1-(2-hydroxyethyl)-6-methoxyquinolin-4(1H)-one that had preliminarily been dissolved in dichloromethane was dropped into this solution for 1 hour, stirring thereof was subsequently conducted overnight. After completion of a reaction, a reaction solution was washed with 0.1 M of hydrochloric acid and a saturated saline and an organic phase was dried over magnesium sulfate. After magnesium sulfate was filtrated and separated, a solvent was removed under a reduced pressure. An obtained residue was fractionated by silica gel chromatography (developing solvent; chloroform:methanol=30:1) to obtain a white powder (S120). An obtained powder was identified by $^1$H NMR as 2,5-dioxopyrolidin-1-yl(2-(6-methoxy-4-oxoquinolin-1(4H)-yl)ethyl) carbonate.

Here, a result of $^1$H NMR measurement was: $^1$H NMR (CD$_3$CN): δ 2.716 (4H, s), 3.882 (3H, s), 4.499 (2H, t, J=5, 5.2 Hz), 4.644 (2H, t, J=4.8, 5 Hz), 6.060 (1H, d, J=7.6 Hz), 7.324 (1H, dd, J=3.2, 9.2 Hz), 7.562 (1H, d, J=9.6 Hz), 7.655 (1H, d, J=7.6 Hz), 7.707 (1H, d, J=2.8 Hz).

(An Example of Synthesis of a Compound for Optical Resolution with Structural Formula (2))

Figure 2:
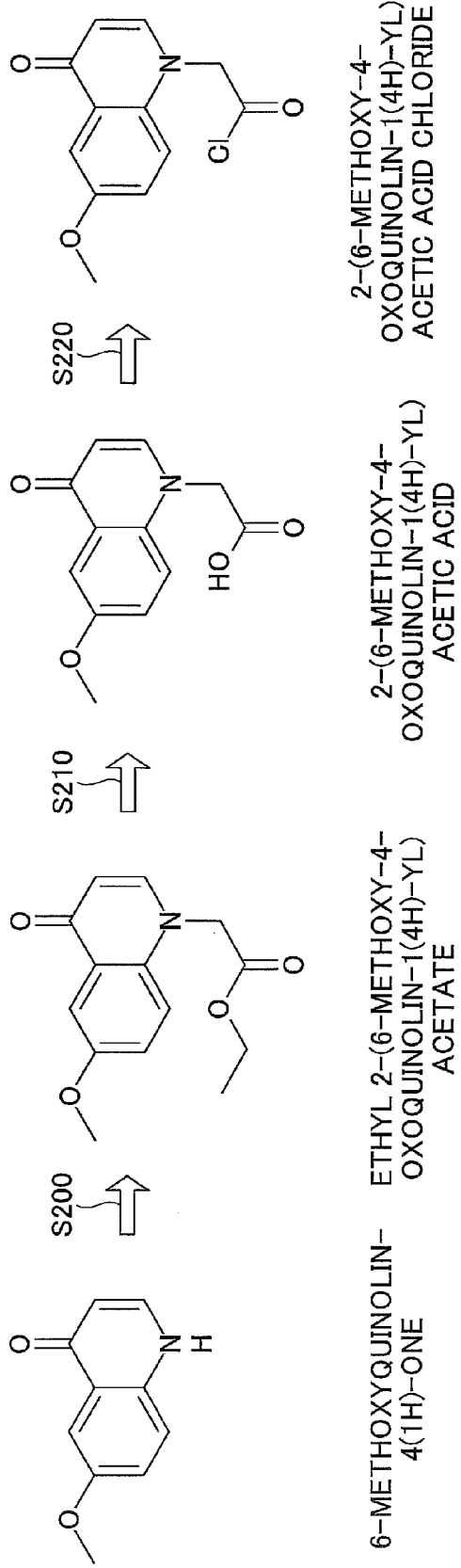
FIG. 2 is another example of a synthetic scheme for a compound for optical resolution according to the present embodiment.

FIG. 2 illustrates another example of a synthetic scheme of a compound for optical resolution according to the present embodiment. A specific example of synthesis of a compound for optical resolution with structural formula (2) described above will be described below, with reference to FIG. 2.

500.5 parts by mass of 6-methoxyquinolin-4(1H)-one, 611.1 parts by mass of potassium carbonate, and 500 μL of ethyl bromoacetate were dissolved in 5 ml of DMF and stirring thereof was conducted overnight. After completion of a reaction, chloroform was added to a reaction solution to conduct filtration and separation, and an obtained product was dried over magnesium sulfate.

After magnesium sulfate was filtrated and separated, an organic solvent was removed under a reduced pressure. An obtained residue was fractionated by silica gel chromatography (developing solvent; chloroform:methanol=15:1→10:1) to obtain a white powder (S200). An obtained powder was identified by $^1$H NMR as ethyl 2-(6-methoxy-4-oxoquinolin-1 (4H)-yl)acetate.

Here, a result of $^1$H NMR measurement was: $^1$H NMR (dmso): δ 1.196 (3H, t, J=7.6 Hz), 3.836 (3H, s), 4.159 (2H, dd, J=7.2, 14 Hz), 5.178 (2H, s), 6.039 (1H, d, J=7.6 Hz), 7.318 (1H, dd, J=2.8, 9.2 Hz), 7.433 (1H, d, J=9.2 Hz), 7.587 (1H, d, J=3.2 Hz), 7.871 (1H, d, J=7.6 Hz).

650 parts by mass of obtained ethyl 2-(6-methoxy-4-oxoquinolin-1(4H)-yl)acetate were dissolved in 5 ml of a 1 M aqueous solution of sodium hydroxide and stirring thereof was conducted overnight. After completion of a reaction, 3 M of hydrochloric acid were added to a reaction solution to filtrate and obtain a precipitate, and subsequently washing with water was conducted to obtain a white powder (S210). An obtained powder was identified by $^1$H NMR as 2-(6-methoxy-4-oxoquinolin-1(4H)-yl)acetic acid.

Here, a result of $^1$H NMR measurement was: $^1$H NMR (dmso): δ 3.835 (3H, s), 5.062 (2H, s), 6.024 (1H, d, J=7.6 Hz), 7.324 (1H, dd, J=3.2, 9.4 Hz), 7.439 (1H, d, J=9.2 Hz), 7.587 (1H, d, J=2.8 Hz), 7.873 (1H, d, J=7.6 Hz), 13.304 (1H, s).

101 parts by mass of obtained 2-(6-methoxy-4-oxoquinolin-1(4H)-yl)acetic acid were dissolved in 700 μL of thionyl chloride and stirring thereof was conducted at 0° C. for 2 hours. After completion of a reaction, thionyl chloride was removed under a reduced pressure and subsequently hexane was added to filtrate and obtain a precipitate, so that a yellow powder was obtained (S220). An obtained powder was identified by $^1$H NMR as 2-(6-methoxy-4-oxoquinolin-1(4H)-yl) acetic acid chloride.

Here, a result of $^1$H NMR measurement was: $^1$H NMR (dmso): δ 3.893 (3H, s), 5.338 (2H, s), 6.611 (1H, d, J=7.2 Hz), 7.520 (18, dd, J=2.8, 9.4 Hz), 7.631 (18, d, J=3.2 Hz), 7.720 (1H, d, J=9.6 Hz), 8.310 (1H, d, J=7.2 Hz).

(An Optically Resolving Method)

Next, a method for optically resolving a mixture of optical isomers of an amino acid by using a compound for optical resolution according to the present embodiment will be described.

Figure 3:
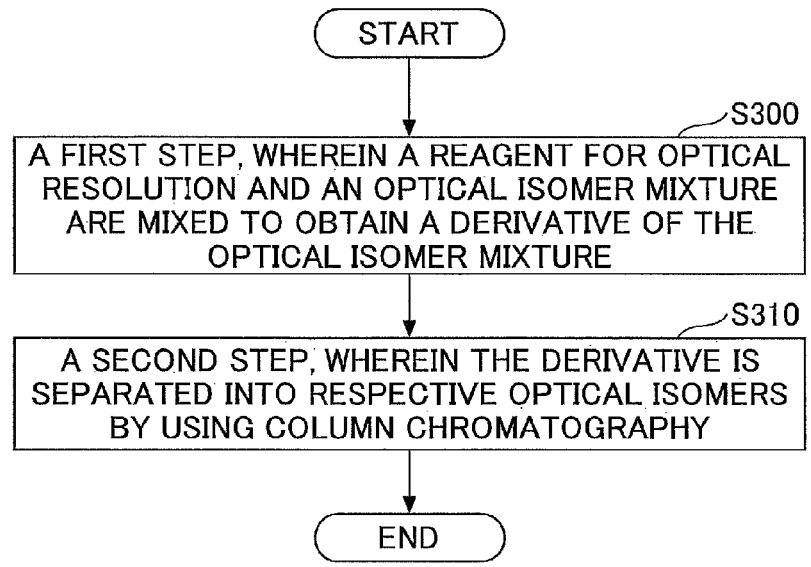
FIG. 3 is a flow diagram of one example of a optically resolving method that uses a compound for optical resolution according to the present embodiment.

FIG. 3 illustrates a flow diagram of one example of an optically resolving method that uses a compound for optical resolution according to the present embodiment.

An optically resolving method according to the present embodiment includes a first step (S300) wherein a reagent for optical resolution and a mixture of optical isomers are mixed to obtain a derivative of the mixture of optical isomers, and a second step (S310) wherein the derivative is separated into respective optical isomers by using column chromatography.

At a first step of S300, a reagent for optical resolution and a mixture of optical isomers are mixed to obtain a derivative of the mixture of optical isomers.

A mixing method is not particularly limited, and for example, it is possible to conduct mixing and reacting thereof at a room temperature for about 1 minute to provide an amino acid derivative. In a case where a conventional reagent for optical resolution is used, it has been necessary to apply heat to and react for a long period of time an amino acid and such a compound for optical resolution in order to prepare an analytical sample. However, in a case where a compound for optical resolution according to the preset embodiment is used, mixing thereof is conducted at a room temperature for about 1 minute so that it is possible to obtain an amino acid derivative, and it is considered that such a method is convenient.

Then, at a second step of S310, a mixture of optical isomers as obtained at the first step is separated into respective optical isomers by using column chromatography.

For a column for column chromatography, it is possible to use a conventional and commercially available column.

Next, an embodiment of the present invention will be described in more detail by providing specific embodiments.

A First Embodiment

In a first embodiment, an embodiment will be described for confirming that an amino acid derivative for which a compound for optical resolution with structural formula (1) described above is used is capable of optical resolution at a good optical resolution performance by HPLC analysis that uses a conventional column.

A compound for optical resolution according to the present embodiment is added to a solution that contains an amino acid as a measurement target and a reaction is caused at a room temperature for about 1 minute, so that it is possible to provide an amino acid derivative for an HPLC measurement.

Specifically, 10 μL of a 40 mM boric acid buffer solution (pH=8) and 5 μL of a solution of a compound for optical resolution with structural formula (1) described above (concentration: 40 mM) are added to 10 μL of an amino acid solution with a predetermined concentration, for example, a concentration of 50 μM, 100 μM, 125 μM, or the like, and mixing thereof is conducted by a vortex mixer for 1 minute, so that it is possible to derivatize an amino acid.

In the first embodiment, 10 μL of a 40 mM boric acid buffer solution (pH=8) and 5 μL of a solution of a compound for optical resolution with formula (1) described above (concentration: 40 mM) were added to 10 μL of an amino acid solution with a concentration of 100 μM, 125 μM, or the like, and mixing thereof was conducted by a vortex mixer for 1 minute, so that an amino acid was derivatized. 475 μL of a 0.5% aqueous solution of trifluoroacetic acid were added to an obtained solution that contained an amino acid derivative to stop a reaction and prepare a sample for HPLC analysis. HPLC analysis was applied to 0.1 μL of an obtained sample. For fluorescence analysis, an excitation wavelength was 243 nm and a fluorescence wavelength was 380 nm, while, for mass spectrometry, for example, mass spectrometry for alanine was conducted for a product ion with a mass-to-charge ratio (M/Z) of 114 produced from a precursor ion with an M/Z of 335.

Analysis conditions for HPLC analysis were:

a column: QN-1AX (1.5 mm i.d.×150 mm);

a flow rate: 200 μL/min;

a temperature: 25° C.;

mobile phase 1 (MP1): 0.02% formic acid methanol/acetonitrile=50/50;

mobile phase 2 (MP2): 0.05% formic acid methanol/acetonitrile=50/50;

mobile phase 3 (MP3): 0.2% formic acid methanol/acetonitrile=50/50;

mobile phase 4 (MP4): 10 mM ammonium formate methanol/acetonitrile=50/50; and mobile phase 5 (MP5): 0.5% formic acid methanol/acetonitrile=50/50.

Table 1 illustrates a summary of kinds of each amino acid and a mobile phase, an elution time for HPLC analysis, elution orders of an L-amino acid and a D-amino acid, and a separation factor α.

TABLE 1

| Kind of amino acid | Kind of mobile phase | First elution time $R_{t1}$ (min) | Second elution time $R_{t2}$ (min) | Early eluted optical isomer | Separation factor α |
|---|---|---|---|---|---|
| Ala | MP1 | 9.15 | 10.477 | D-body | 1.157 |
| Asn | MP1 | 13.48 | 14.733 | D-body | 1.098 |
| Gln | MP1 | 12.28 | 13.73 | D-body | 1.125 |
| Trp | MP2 | 9.52 | 11.933 | D-body | 1.274 |
| Asp | MP5 | 13.097 | 13.937 | D-body | 1.068 |
| Glu | MP3 | 5.53 | 6.58 | D-body | 1.22 |
| Ser | MP2 | 11.733 | 13.837 | D-body | 1.191 |
| Thr | MP2 | 9.12 | 11.51 | D-body | 1.284 |
| allo-Thr | MP2 | 12.033 | 16.253 | D-body | 1.372 |
| Tyr | MP2 | 10.403 | 12.137 | D-body | 1.179 |
| Phe | MP1 | 9.25 | 10.77 | D-body | 1.179 |
| Val | MP1 | 7.943 | 10.213 | D-body | 1.313 |
| Leu | MP1 | 6.597 | 8.208 | D-body | 1.285 |
| Ile | MP1 | 7.44 | 9.633 | D-body | 1.325 |
| all-Ile | MP1 | 7.813 | 10.17 | D-body | 1.33 |
| Cys | MP2 | 20.81 | 24.97 | D-body | 1.207 |
| Met | MP1 | 12.593 | 15.357 | D-body | 1.232 |
| Cystine (CysCys) | MP5 | 13.643 | 19.173 | D-body | 1.427 |
| Lys | MP1 | 6.723 | 8.073 | D-body | 1.224 |
| His | MP4 | 5.323 | 6.127 | D-body | 1.174 |

As is clear from Table 1, a separation factor α of an amino acid derivatized by a compound for optical resolution according to the present embodiment was greater than or equal to 1.07 independently of a kind thereof (for example, a neutral amino acid, an acidic amino acid, a hydrophobic amino acid, a sulfur-containing amino acid, a basic amino acid, or the like).

Furthermore, a detection limit of an optically resolving method that used a compound for optical resolution according to the present embodiment was at a femt mol order—an atto mol order per an amount of injection and was very highly sensitive as compared to that of a conventional method.

From the above, it was found that a compound for optical resolution according to the present embodiment was used to prepare an amino acid derivative and this was analyzed by HPLC, so that it was possible to optically resolve a mixture of optical isomers of an amino acid at a high resolution and a high detection sensitivity by a convenient method.

A Second Embodiment

Furthermore, an embodiment will be described for evidencing that an effect of a compound for optical resolution according to the present embodiment is independent on a kind of a column and is also capable of being applied to another conventional column.

Predetermined amino acids were optically resolved by a method similar to that of the first embodiment except that analysis conditions for HPLC analysis were changed to the following and kinds of amino acids were changed partially.

Analysis conditions for HPLC analysis were:
a column: QD-1AX (1.5 mm i.d.×150 mm);
a flow rate: 200 μL/min;
a temperature: 25° C.;
mobile phase 1 (MP1): 0.02% formic acid methanol/acetonitrile=50/50;
mobile phase 2 (MP2): 0.05% formic acid methanol/acetonitrile=50/50;
mobile phase 3 (MP3): 0.25% formic acid methanol/acetonitrile=50/50;
mobile phase 4 (MP4): 10 mM ammonium formate that contained 0.032% formic acid methanol/acetonitrile=20/80;
mobile phase 5 (MP5): 0.5% formic acid methanol/acetonitrile=50/50; and
mobile phase 6 (MP6): 1% formic acid methanol/acetonitrile=50/50.

Table 2 illustrates a summary of kinds of each amino acid and a mobile phase, an elution time for HPLC analysis, elution orders of an L-amino acid and a D-amino acid, and a separation factor α.

TABLE 2

| Kind of amino acid | Kind of mobile phase | First elution time $R_{t1}$ (min) | Second elution time $R_{t2}$ (min) | Early eluted optical isomer | Separation factor α |
|---|---|---|---|---|---|
| Ala | MP1 | 9.307 | 11.757 | L-body | 1.285 |
| Asn | MP1 | 14.037 | 15.82 | L-body | 1.134 |
| Gln | MP1 | 12.99 | 15.557 | L-body | 1.209 |
| Trp | MP2 | 10.553 | 13.677 | L-body | 1.317 |
| Asp | MP3 | 14.483 | 16.567 | L-body | 1.151 |
| Glu | MP3 | 6.577 | 8.737 | L-body | 1.368 |
| Ser | MP2 | 12.413 | 16.623 | L-body | 1.359 |
| Thr | MP2 | 10.317 | 13.873 | L-body | 1.37 |
| allo-Thr | MP2 | 12.833 | 19.237 | L-body | 1.528 |
| Tyr | MP2 | 10.913 | 14.18 | L-body | 1.32 |
| Phe | MP1 | 15.657 | 20.197 | L-body | 1.304 |
| Val | MP1 | 7.74 | 10.43 | L-body | 1.382 |
| Leu | MP1 | 6.423 | 8.743 | L-body | 1.405 |
| Ile | MP1 | 7.163 | 9.983 | L-body | 1.436 |
| all-Ile | MP1 | 7.427 | 10.193 | L-body | 1.411 |
| Cys | MP5 | 7.21 | 8.94 | L-body | 1.266 |
| Met | MP1 | 13.177 | 17.66 | L-body | 1.359 |
| Cystine (CysCys) | MP6 | 4.6 | 6.833 | L-body | 1.573 |
| Arg | MP4 | 6.087 | 7.037 | L-body | 1.18 |
| Lys | MP1 | 8.06 | 9.48 | L-body | 1.193 |
| His | MP4 | 10.14 | 12.67 | L-body | 1.267 |

Furthermore, predetermined amino acids were optically resolved by a method similar to that of the first embodiment except that analysis conditions for HPLC analysis were changed to the following and kinds of amino acids were changed partially.

Analysis conditions for HPLC analysis were:
a column: Sumichiral OA-3200S (1.5 mm i.d.×250 nmm);
a flow rate: 200 μL/min;
a temperature: 25° C.;
mobile phase 1 (MP1): 0.05% formic acid methanol/acetonitrile=50/50;
mobile phase 2 (MP2): 0.1% formic acid methanol/acetonitrile=50/50;
mobile phase 3 (MP3): 0.05% formic acid methanol/acetonitrile=50/50; and
mobile phase 4 (MP4): 0.25% formic acid methanol/acetonitrile=50/50.

Table 3 illustrates a sunmary of kinds of each amino acid and a mobile phase, an elution time for HPLC analysis, elution orders of an L-amino acid and a D-amino acid, and a separation factor α.

TABLE 3

| Kind of amino acid | Kind of mobile phase | First elution time $R_{t1}$ (min) | Second elution time $R_{t2}$ (min) | Early eluted optical isomer | Separation factor α |
|---|---|---|---|---|---|
| Ala | MP1 | 11.097 | 11.473 | D-body | 1.038 |
| Asn | MP2 | 12.49497 | 13.033 | D-body | 1.048 |
| Ser | MP2 | 12.23 | 12.95 | D-body | 1.065 |
| Thr | MP2 | 9.333 | 10.04 | D-body | 1.087 |
| Val | MP1 | 8.44 | 8.89 | D-body | 1.062 |

TABLE 3-continued

| Kind of amino acid | Kind of mobile phase | First elution time $R_{t1}$ (min) | Second elution time $R_{t2}$ (min) | Early eluted optical isomer | Separation factor α |
|---|---|---|---|---|---|
| Leu | MP1 | 7.26 | 8.003 | D-body | 1.123 |
| Ile | MP1 | 7.803 | 8.227 | D-body | 1.064 |
| all-Ile | MP1 | 7.783 | 8.63 | | 1.129 |
| Cys | MP2 | 25.877 | 26.8 | D-body | 1.037 |
| Met | MP1 | 11.953 | 12.93 | D-body | 1.091 |
| Cystine (CysCys) | MP3 | 19.573 | 20.157 | D-body | 1.032 |
| Lys | MP1 | 11.58 | 12.413 | D-body | 1.08 |

Moreover, predetermined amino acids were optically resolved by a method similar to that of the first embodiment except that analysis conditions for HPLC analysis were changed to the following and kinds of amino acids were changed partially.

Analysis conditions for HPLC analysis were:

a column: Sumichiral OA-4700SR (1.5 mm i.d.×250 mm);

a flow rate: 200 μL/min;

a temperature: 25° C.;

mobile phase 1 (MP1): 0.02% formic acid methanol/acetonitrile=50/50; and mobile phase 2 (MP2): 0.05% formic acid methanol/acetonitrile=50/50.

Table 4 illustrates a summnary of kinds of each amino acid and a mobile phase, an elution time for HPLC analysis, elution orders of an L-amino acid and a D-amino acid, and a separation factor α.

TABLE 4

| Kind of amino acid | Kind of mobile phase | First elution time $R_{t1}$ (min) | Second elution time $R_{t2}$ (min) | Early eluted optical isomer | Separation factor α |
|---|---|---|---|---|---|
| allo-Thr | MP2 | 11.763 | 12.507 | D-body | 1.071 |
| Phe | MP1 | 13.463 | 14.433 | D-body | 1.079 |
| Val | MP1 | 8.713 | 9.383 | D-body | 1.089 |
| Leu | MP1 | 6.747 | 7.62 | D-body | 1.157 |
| Ile | MP1 | 7.54 | 8.357 | D-body | 1.129 |
| all-Ile | MP1 | 7.875 | 8.81 | D-body | 1.143 |
| Met | MP1 | 12.183 | 13.363 | D-body | 1.107 |
| Lys | MP1 | 8.257 | 9.277 | D-body | 1.145 |

Moreover, predetermined amino acids were optically resolved by a method similar to that of the first embodiment except that analysis conditions for HPLC analysis were changed to the following and kinds of amino acids were changed partially.

Analysis conditions for HPLC analysis were:

a column: KSAACSP-001S (1.5 mm i.d.×250 mm);

a flow rate: 200 μL/min;

a temperature: 25° C.;

mobile phase 1 (MP1): 0.05% formic acid methanol/acetonitrile=50/50;

mobile phase 2 (MP2): 0.1% formic acid methanol/acetonitrile=50/50; and mobile phase 3 (MP3): 5 mM solution of ammonium formate in methanol (flow rate: 150 μL/min).

Table 5 illustrates a summary of kinds of each amino acid and a mobile phase, an elution time for HPLC analysis, elution orders of an L-amino acid and a D-amino acid, and a separation factor α.

TABLE 5

| Kind of amino acid | Kind of mobile phase | First elution time $R_{t1}$ (min) | Second elution time $R_{t2}$ (min) | Early eluted optical isomer | Separation factor α |
|---|---|---|---|---|---|
| Pro | MP1 | 13.82 | 14.873 | L-body | 1.084 |
| Trp | MP2 | 7.577 | 8.24 | L-body | 1.104 |
| Ser | MP2 | 13.043 | 13.583 | D-body | 1.046 |
| Thr | MP2 | 9.473 | 9.977 | D-body | 1.061 |
| allo-Thr | MP2 | 12.373 | 13.003 | L-body | 1.056 |
| Phe | MP1 | 12.357 | 13.133 | L-body | 1.07 |
| Val | MP1 | 8.287 | 8.887 | L-body | 1.086 |
| Ile | MP1 | 7.89 | 8.597 | L-body | 1.107 |
| all-Ile | MP1 | 7.5 | 8.133 | L-body | 1.102 |
| Met | MP1 | 11.303 | 11.737 | L-body | 1.091 |
| Arg | MP3 | 11.607 | 11.96 | L-body | 1.04 |
| Lys | MP1 | 12.92 | 13.877 | L-body | 1.082 |

As is clear from results of Table 1 and Table 2 to Table 5, a separation factor α of an amino acid derivatized by a compound for optical resolution according to the present embodiment was greater than or equal to 1 independently of a kind of a column or a kind of an amino acid.

From the above, it was found that a compound for optical resolution according to the present embodiment was used to prepare an amino acid derivative and this was analyzed by HPLC that used a conventional column, so that it was possible to optically resolve a mixture of optical isomers of an amino acid at a high resolution and a high detection sensitivity by a convenient method.

A Third Embodiment

In a third embodiment, an embodiment will be described for confirming that an amino acid derivative for which a compound for optical resolution with structural formula (2) described above is used is capable of optical resolution by HPLC analysis that uses a conventional column.

Alanine was derivatized by a method similar to that of the first embodiment except that a compound with structural formula (2) was used as a compound for optical resolution.

HPLC analysis was applied to 0.1 μL of an obtained sample. For fluorescence analysis, an excitation wavelength was 243 nm and a fluorescence wavelength was 380 nm, while, for mass spectrometry, mass spectrometry was conducted for a product ion with a mass-to-charge ratio (M/Z) of 259 produced from a precursor ion with an M/Z of 305.

Analysis conditions for HPLC analysis were:

a column: QN-AX (1.5 mm i.d.×150 mm);

a flow rate: 200 μL/min;

a temperature: 25° C.; and a mobile phase: 0.05% formic acid methanol/acetonitrile=50/50.

Figure 4:
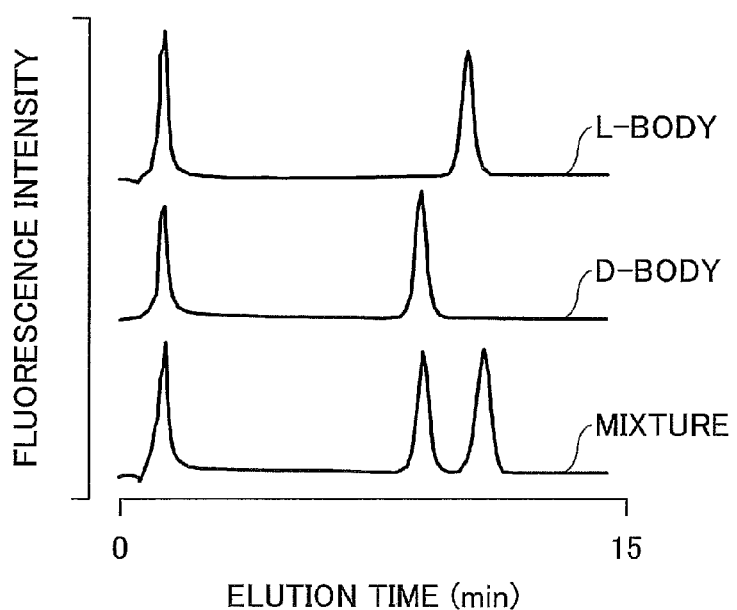
FIG. 4 is one example of a result of HPLC-FD analysis that uses a compound for optical resolution according to the present embodiment.
Figure 5:
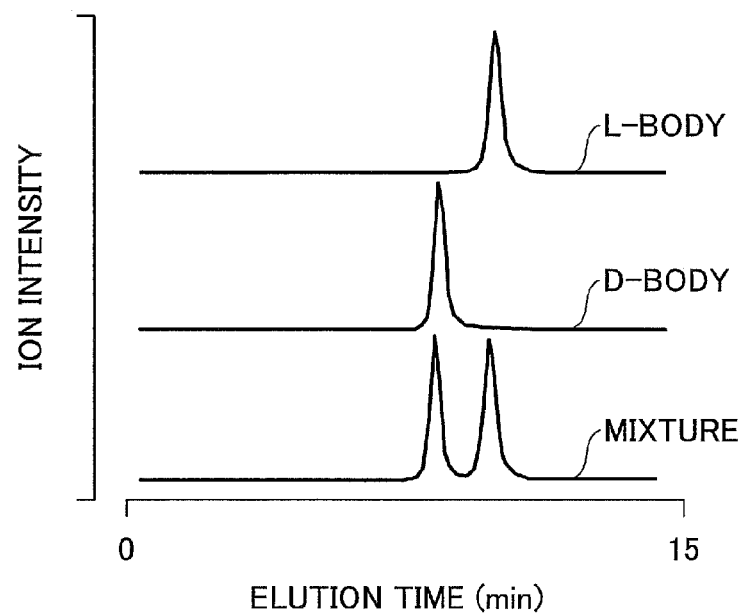
FIG. 5 is one example of a result of HPLC-MS analysis that uses a compound for optical resolution according to the present embodiment.

FIG. 4 illustrates one example of a result of HPLC-FL analysis and FIG. 5 illustrates one example of a result of HPLC-MS analysis. In FIG. 4, a transverse axis indicates an elution time and a longitudinal axis indicates a fluorescence intensity. Furthermore, in FIG. 5, a transverse axis indicates an elution time and a longitudinal axis indicates an ion intensity. Furthermore, FIG. 4 and FIG. 5 indicate, in combination, results of cases where only an L-body or a D-body was subjected to a similar analysis.

As is clear from FIG. 4 and FIG. 5, it was found in any result of analysis that a compound for optical resolution according to the present embodiment was used so that it was possible to separate a mixture of optical isomers completely.

Furthermore, a detection limit of an optically resolving method that used a compound for optical resolution according to the present embodiment was at a femt mol order—an atto mol order per an amount of injection and was very highly sensitive as compared to that of a conventional method.

From the above, it was found that a compound for optical resolution according to the present embodiment was used to prepare an amino acid derivative and this was analyzed by HPLC, so that it was possible to optically resolve a mixture of optical isomers of an amino acid at a high resolution and a high detection sensitivity by a convenient method.

A Fourth Embodiment

It is very important to derivatize an amino acid easily for a short period of time in a technical field where an amino acid is derivatized and analyzed by HPLC. In a fourth embodiment, an embodiment will be described for confirming that it is possible for a compound for optical resolution according to the present embodiment to derivatize an amino acid for a short period of time.

10 µL of a 40 mM boric acid buffer solution (pH=8) and 5 µL of a solution of a compound for optical resolution with structural formula (1) described above (concentration: 40 mM) were added to 10 µL of an L-alanine solution with a concentration of 50 µM. This solution was mixed by a vortex mixer for 1, 2, 5, or 10 minutes to derivatize an amino acid. 475 µL of a 0.5% aqueous solution of trifluoroacetic acid were added to an obtained solution that contained an amino acid derivative to stop a reaction and prepare a sample for HPLC analysis. Furthermore, for a comparative embodiment, 475 µL of a 0.5% aqueous solution of trifluoroacetic acid were added without passing through mixing by a vortex mixer to prepare a sample for HPLC analysis.

HPLC analysis was applied to 0.1 µL of an obtained sample similarly to the first embodiment. For fluorescence analysis, an excitation wavelength was 243 nm and a fluorescence wavelength was 380 nm, while, for mass spectrometry, mass spectrometry was conducted for a product ion with a mass-to-charge ratio (M/Z) of 114 produced from a precursor ion with an M/Z of 335.

Figure 6:
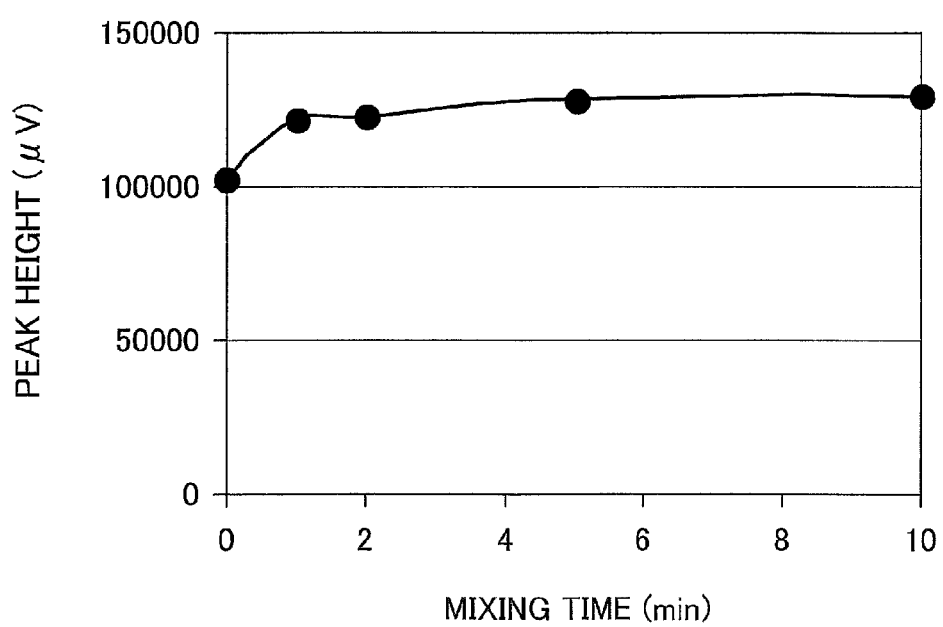
FIG. 6 is a schematic diagram for illustrating one example of an effect of a compound for optical resolution according to the present embodiment.

A schematic diagram for illustrating one example of an effect of a compound for optical resolution according to the present embodiment is illustrated in FIG. 6. In FIG. 6, a transverse axis is for a mixing time for a compound for optical resolution and L-alanine and a longitudinal axis is for a peak height (µV) originating from an L-alanine derivative.

As illustrated in FIG. 6, a change of a peak height was hardly observed for a sample with a mixing time of 1 minute to 10 minutes whereas a change of a peak height was observed between a sample with a mixing time of 0 minutes and a sample with that of 1 minute to 10 minutes. Accordingly, it was found that it was possible for a compound for optical resolution according to the present embodiment to derivatize an amino acid by only being mixed with such an amino acid for about 1 minute.

A Fifth Embodiment

In a fifth embodiment, an embodiment will be described for confirming that an amino acid derivative obtained by reacting a compound for optical resolution according to the present embodiment with an amino acid has an excellent heat stability.

10 µL of a 40 mM boric acid buffer solution (pH=8) and 5 µL of a solution of a compound for optical resolution with structural formula (1) described above (concentration: 40 mM) were added to 10 µL of an L-alanine solution with a concentration of 50 µM. This solution was mixed by a vortex mixer for 1 minute to derivatize an amino acid. 475 µL of a 0.5% aqueous solution of trifluoroacetic acid were added to an obtained solution that contained an amino acid derivative to prepare a sample for HPLC analysis.

50 µL of an obtained sample for HPLC analysis were heated for 5, 10, 20, 30, or 60 minutes by using an aluminum heater that was set at 50° C. preliminarily. HPLC analysis was applied to 0.1 µL of a sample after heating similarly to the first embodiment. For fluorescence analysis, an excitation wavelength was 243 nm and a fluorescence wavelength was 380 nm, while, for mass spectrometry, mass spectrometry was conducted for a product ion with a mass-to-charge ratio (M/Z) of 114 produced from a precursor ion with an M/Z of 335.

Figure 7:
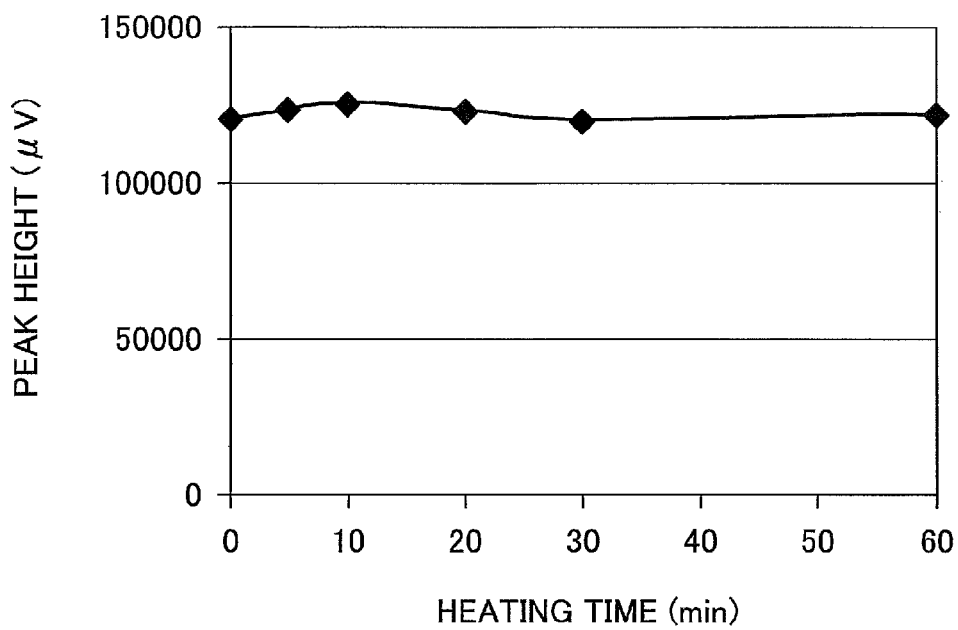
FIG. 7 is a schematic diagram for illustrating another example of an effect of a compound for optical resolution according to the present embodiment.

A schematic diagram for illustrating another example of an effect of a compound for optical resolution according to the present embodiment is illustrated in FIG. 7. In FIG. 7, a transverse axis is for a heating time for an L-alanine derivative and a longitudinal axis is for a peak height (µV) originating from such an L-alanine derivative.

As illustrated in FIG. 7, reduction of an L-alanine derivative was not confirmed within a range of a heating time in the present embodiment. Accordingly, it was found that an amino acid derivative obtained by using a compound for optical resolution according to the present embodiment has an excellent heat stability.

A Sixth Embodiment

In a sixth embodiment, an embodiment will be described for confirming that an amino acid derivative obtained by reacting a compound for optical resolution according to the present embodiment with an amino acid has an excellent light stability.

10 µL of a 40 mM boric acid buffer solution (pH=8) and 5 µL of a solution of a compound for optical resolution with structural formula (1) described above (concentration: 40 mM) were added to 10 µL of an L-alanine solution with a concentration of 50 µM. This solution was mixed by a vortex mixer for 1 minute to derivatize an amino acid. 475 µL of a 0.5% aqueous solution of trifluoroacetic acid were added to an obtained solution that contained an amino acid derivative to prepare a sample for HPLC analysis.

An obtained sample for HPLC analysis was stood for 0.5, 1, 2, 3, or 5 hours under light irradiation by a fluorescent lamp. HPLC analysis was applied to 0.1 µL of a sample after standing similarly to the first embodiment. For fluorescence analysis, an excitation wavelength was 243 nm and a fluorescence wavelength was 380 nm, while, for mass spectrometry, mass spectrometry was conducted for a product ion with a mass-to-charge ratio (M/Z) of 114 produced from a precursor ion with an M/Z of 335.

Figure 8:
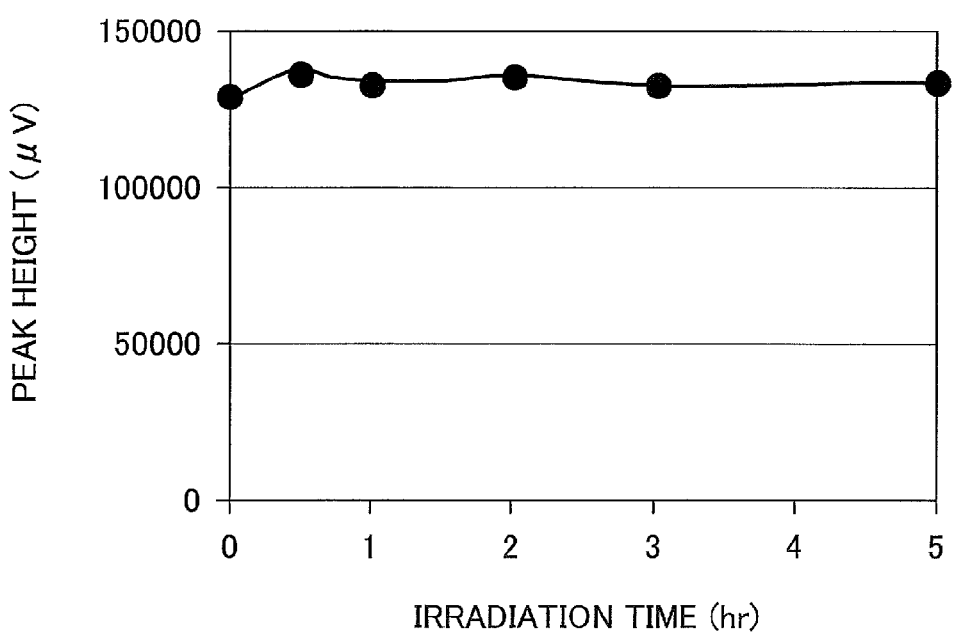
FIG. 8 is a schematic diagram for illustrating another example of an effect of a compound for optical resolution according to the present embodiment.

A schematic diagram for illustrating another example of an effect of a compound for optical resolution according to the present embodiment is illustrated in FIG. 8. In FIG. 8, a transverse axis is for an irradiation time for an L-alanine derivative and a longitudinal axis is for a peak height (µV) originating from such an L-alanine derivative.

As illustrated in FIG. 8, reduction of an L-alanine derivative was not confirmed within ranges of an irradiation intensity and an irradiation time in the present embodiment. Accordingly, it was found that an amino acid derivative obtained by using a compound for optical resolution according to the present embodiment has an excellent light stability.

From the above, it was found that it was possible to mix a compound for optical resolution according to the present embodiment with a mixture of optical isomers of an amino acid to prepare an amino acid derivative, and this was analyzed by HPLC in such a manner that it was possible to optically resolve a mixture of optical isomers at a high resolution and a high detection sensitivity by a convenient method. At this time, it was found that a mixture of optical isomers of an amino acid was derivatized by mixing at a room temperature for about 1 minute. Furthermore, it was found that an obtained amino acid derivative was excellent in a heat stability and a light stability.

APPENDIX

An Illustrative Embodiment(s) of a Compound for Optical Resolution, a Reagent for Optical Resolution, an Optically Resolving Method, and an Optical Isomer At least one illustrative embodiment of the present invention may relate to a compound for optical resolution, a reagent for optical resolution, an optically resolving method, and an optical isomer.

At least one illustrative embodiment of the present invention may aim at providing a compound for optical resolution that is capable of optically resolving a mixture of optical isomers of an amino acid conveniently at a high sensitivity, against a problem as described above.

At least one illustrative embodiment of the present invention may be provided as a compound for optical resolution that is a structural formula (1):

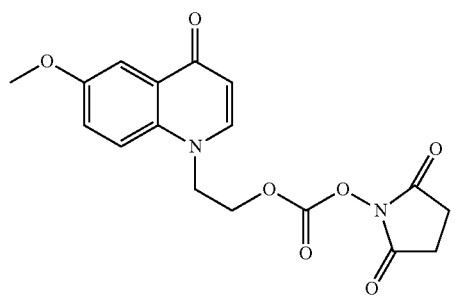 [SMILES: COc1ccc2c(c1)c(=O)ccn2CCOC(=O)ON1C(=O)CCC1=O]

or structural formula (2):

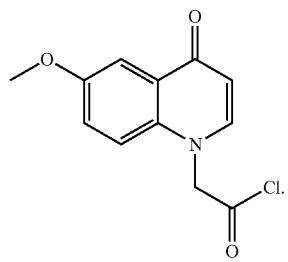 [SMILES: COc1ccc2c(c1)c(=O)ccn2CC(=O)Cl]

Illustrative embodiment (1) is a compound for optical resolution that is structural formula (1):

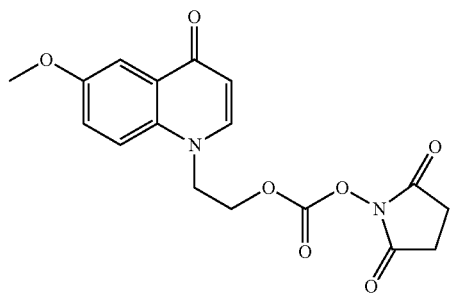 [SMILES: COc1ccc2c(c1)c(=O)ccn2CCOC(=O)ON1C(=O)CCC1=O]

or structural formula (2):

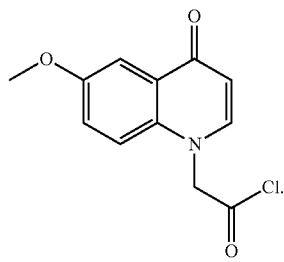 [SMILES: COc1ccc2c(c1)c(=O)ccn2CC(=O)Cl]

Illustrative embodiment (2) is a reagent for optical resolution, that includes the compound for optical resolution as described in illustrative embodiment (1).

Illustrative embodiment (3) is a method for optically resolving a mixture of optical isomers of an amino acid, that uses the reagent for optical resolution as described in illustrative embodiment (2).

Illustrative embodiment (4) is the method for optically resolving as described in illustrative embodiment (3), that includes a first step of mixing the reagent for optical resolution and the mixture of optical isomers to obtain a derivative of the mixture of optical isomers.

Illustrative embodiment (5) is the method for optically resolving as described in illustrative embodiment (4), wherein the first step includes a step of mixing at a room temperature for one minute.

Illustrative embodiment (6) is the method for optically resolving as described in illustrative embodiment (4) or (5), that includes a second step of separating the derivative into respective optical isomers by using column chromatography after the first step.

Illustrative embodiment (7) is an optical isomer of an amino acid that is obtained by the method for optically resolving as described in any one of illustrative embodiments (4) to (6).

According to at least one illustrative embodiment of the present invention, it may be possible to provide a compound for optical resolution that is capable of optically resolving a mixture of optical isomers of an amino acid conveniently at a high sensitivity.

Although the illustrative embodiment(s) and specific example(s) of the present invention have been described with reference to the accompanying drawings, the present invention is not limited to any of the illustrative embodiment(s) and specific example(s) and the illustrative embodiment(s) and specific example(s) may be altered, modified, or combined without departing from the scope of the present invention.

The present application is based on and claims the benefit of priority to Japanese Patent Application No. 2013-181305 filed on Sep. 2, 2013, the entire content of which is herein incorporated by reference herein.
What is claimed is:
1. A compound represented by chemical formula (1):
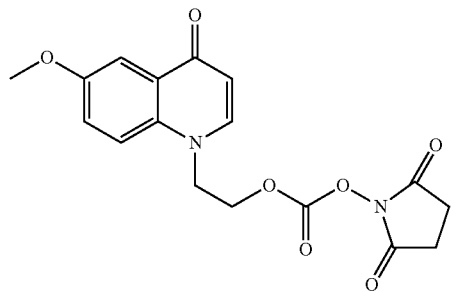 [SMILES: COc1ccc2c(c1)c(=O)ccn2CCOC(=O)ON1C(=O)CCC1=O]
or chemical formula (2):
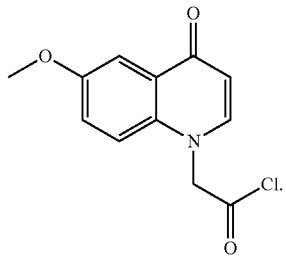 [SMILES: COc1ccc2c(c1)c(=O)ccn2CC(=O)Cl]
* * * * *